United States Patent
Zhang et al.

(10) Patent No.: US 6,577,904 B1
(45) Date of Patent: Jun. 10, 2003

(54) ULTRASOUND ECHOGENIC CARDIAC LEAD

(75) Inventors: Yongxing Zhang, Little Canada, MN (US); Mohan Krishnan, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/538,675

(22) Filed: Mar. 30, 2000

(51) Int. Cl.[7] .................................................. A61N 1/00
(52) U.S. Cl. ...................................................... 607/116
(58) Field of Search ................................. 607/122–129, 607/116, 131

(56) References Cited

U.S. PATENT DOCUMENTS

| | | | |
|---|---|---|---|
| 4,249,539 A | 2/1981 | Vilkomerson et al. | 128/660 |
| 4,697,595 A | 10/1987 | Breyer et al. | 128/660 |
| 4,706,681 A | 11/1987 | Breyer et al. | 128/642 |
| 4,739,768 A | 4/1988 | Engelson | 128/658 |
| 4,907,973 A | 3/1990 | Hon | 434/262 |
| 5,081,997 A | 1/1992 | Bosley, Jr. et al. | 128/662.02 |
| 5,095,910 A | 3/1992 | Powers | 128/662.05 |
| 5,131,397 A | 7/1992 | Crowley | 128/662.06 |
| 5,161,536 A | 11/1992 | Vilkomerson et al. | 128/660.07 |
| 5,289,831 A | 3/1994 | Bosley | 128/899 |
| 5,318,025 A | 6/1994 | Dumoulin et al. | 128/653.2 |
| 5,323,781 A | 6/1994 | Ideker et al. | 128/660.03 |
| 5,325,860 A | 7/1994 | Seward et al. | 128/662.06 |
| 5,343,865 A | 9/1994 | Gardineer et al. | 128/662.05 |
| 5,345,940 A | 9/1994 | Seward et al. | 128/662.06 |
| 5,374,287 A | * 12/1994 | Rubin | 607/122 |
| 5,391,199 A | 2/1995 | Ben-Haim | 607/122 |
| 5,433,198 A | 7/1995 | Desai | 128/642 |
| 5,445,150 A | 8/1995 | Dumoulin et al. | 128/653.1 |
| 5,464,016 A | 11/1995 | Nicholas et al. | 128/662.06 |
| 5,538,004 A | 7/1996 | Bamber | 128/662.06 |
| 5,546,951 A | 8/1996 | Ben-Haim | 128/702 |
| 5,577,502 A | 11/1996 | Darrow et al. | 128/653.1 |
| 5,921,933 A | * 7/1999 | Sarkis et al. | 600/459 |
| 6,083,216 A | * 7/2000 | Fischer, Sr. | 600/374 |
| 6,106,473 A | * 8/2000 | Violante et al. | 427/2.11 |

OTHER PUBLICATIONS

Langberg, J.L., et al., "The Echo–Transponder Electrode Catheter: A New Method for Mapping the Left Ventricle", *JACC, 12 (1)*, pp. 218–223, (Jul. 1998).

* cited by examiner

*Primary Examiner*—Mark Bockelman
(74) *Attorney, Agent, or Firm*—Schwegman, Lundberg, Woessner & Kluth, P.A.

(57) ABSTRACT

A lead has a flexible lead body which extends from a proximal end to a distal end. The lead body has a conductor coupled with an electrode. At least a portion of the conductor includes a layer of echogenic material encapsulated by the lead body. Alternatively, the echogenic material includes a coating of material. Optionally, the layer of echogenic material is disposed on at least a portion of the conductor or on one or more portions of the conductor.

21 Claims, 4 Drawing Sheets ially to leads implanted
ULTRASOUND ECHOGENIC CARDIAC LEAD

TECHNICAL FIELD

The present invention relates generally to leads implanted in the heart and for conducting electrical signals to and from the heart. More particularly, it pertains to an ultrasound echogenic cardiac lead.

TECHNICAL BACKGROUND

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle.

Cardiac pacing may be performed by the transvenous method or by leads implanted directly onto the ventricular epicardium. Permanent transvenous pacing is performed using a lead positioned within one or more chambers of the heart. A lead may be positioned in the ventricle or in the atrium through a subclavian vein, or cephalic vein, and the lead terminal pins are attached to a pacemaker which is implanted subcutaneously or submuscularly.

As the leads are implanted, or after the leads are implanted, the leads can be monitored using fluoroscopy. However, some hospitals or other places at which implantation of leads occurs have limited or no access to fluoroscopic equipment, for instance in countries with limited economic means. In addition, some patients should not be treated using fluoroscopy, for instance, women in early stages of pregnancy.

Accordingly, there is a need for a lead which allows for monitoring of the lead during or after implantation of the lead. What is also needed is a lead which allows for monitoring of the lead without substantial risk to the patient.

SUMMARY

A lead assembly is provided including a flexible lead body extending from a proximal end to a distal end. The lead body has at least one conductor and a layer of echogenic material disposed directly on or in the conductor or directly on an inner surface of the conductor. Optionally, the conductor includes a helix forming an active fixation device disposed at the distal end of the lead body, where the echogenic material is disposed on the helix.

The flexible lead body has an outer surface, where the layer of echogenic material is completely encapsulated by the flexible lead body. An electrode assembly has at least one electrode which is electrically coupled with the conductor. In one alternative, the lead assembly includes an inner layer of insulator, and the echogenic material is disposed between the conductor and the inner layer of insulator. In another alternative, the conductor comprises one or more filars, each filar having an outer filar surface, the echogenic material disposed directly on at least a portion of the outer filar surface. In yet another option, the echogenic material is disposed on one or more portions of a length of the lead. Optionally, the echogenic material comprises an echogenic coating. The echogenic coating optionally comprises a porous coating, a metallic coating, or a metal oxide coating.

A lead assembly is provided including a flexible lead body extending from a proximal end to a distal end. The lead body has at least one conductor and a layer of echogenic material disposed directly on or in the conductor. The conductor comprises one or more filars, each filar having an outer filar surface, the echogenic material disposed directly on at least a portion of the outer filar surface. Optionally, the conductor includes a helix forming an active fixation device disposed at the distal end of the lead body, where the echogenic material is disposed on the helix.

The flexible lead body has an outer surface, where the layer of echogenic material is completely encapsulated by the flexible lead body. An electrode assembly has at least one electrode which is electrically coupled with the conductor.

In one alternative, the lead assembly includes an inner layer of insulator, and the echogenic material is disposed between the conductor and the inner layer of insulator. In yet another option, the echogenic material is disposed on one or more portions of a length of the lead.

Optionally, the echogenic material comprises an echogenic coating. The echogenic coating optionally comprises a porous coating, a metallic coating, or a metal oxide coating.

A lead assembly is provided including a flexible lead body extending from a proximal end to a distal end. The lead body has at least one conductor and a layer of echogenic material disposed directly on or in the conductor. The echogenic material is disposed on one or more portions of a length of the lead.

Optionally, the conductor includes a helix forming an active fixation device disposed at the distal end of the lead body, where the echogenic material is disposed on the helix.

The lead includes a layer of echogenic material which provides a cost effective alternative to monitoring an implanted medical device, such as a lead. The echogenic material also allows the lead to be monitored safely, without risk to patients having sensitive medical conditions. In addition, the layer of echogenic material is encapsulated by the lead body, such that the exposed blood and tissue contact surfaces of the lead remain unaffected from long-term biocompatibility and biostability.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
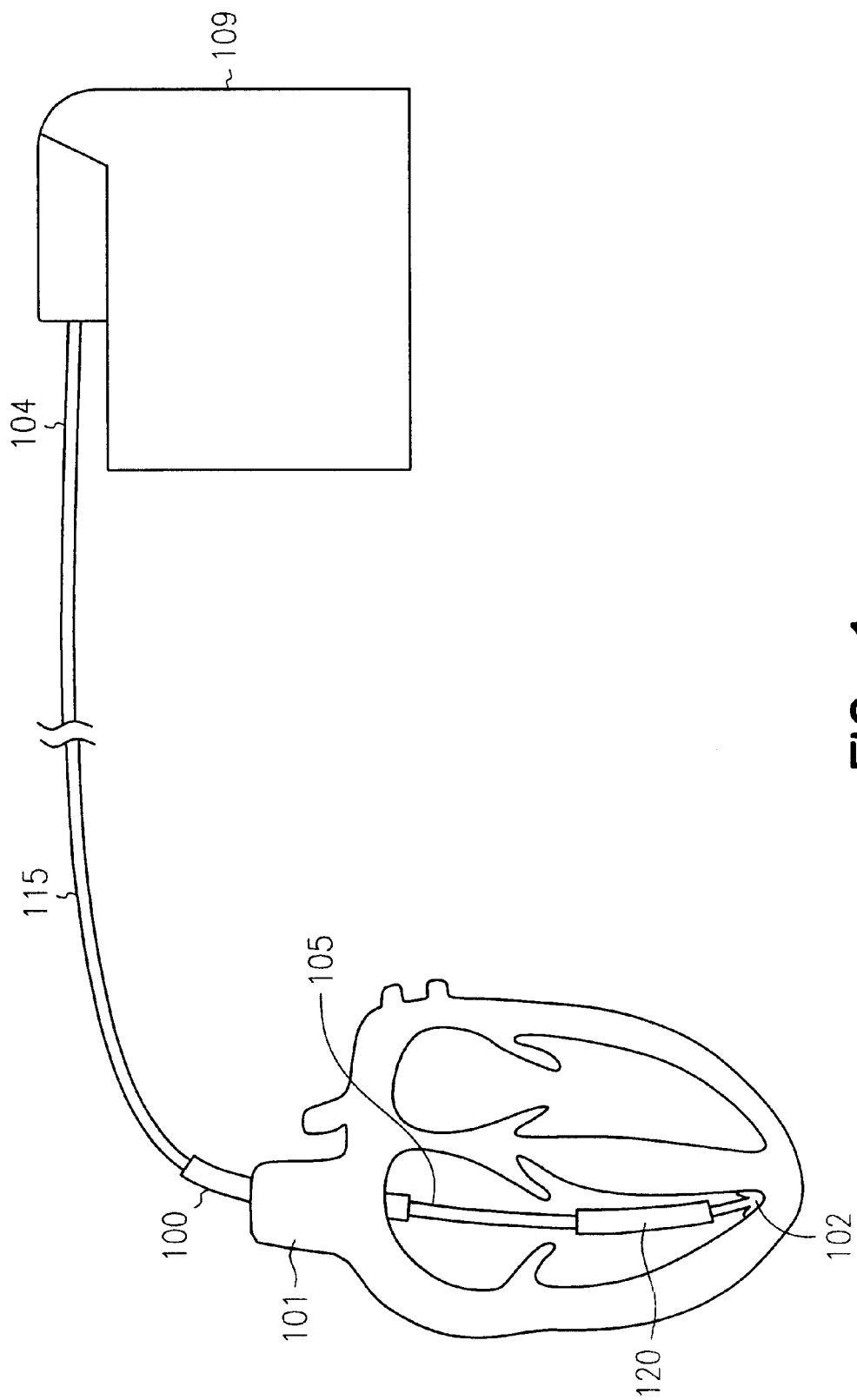
FIG. 1 illustrates a system for monitoring and stimulating the heart constructed in accordance with one embodiment.

FIG. 1 illustrates a single-pass lead 100 for delivering electrical pulses to stimulate a heart 101 and/or for receiving electrical pulses to monitor the heart 101. The lead 100 extends from a distal end 102 to a proximal end 104, and has an intermediate portion 105 therebetween. The distal end 102 is adapted for implantation within the heart of a patient, the proximal end 104 has a terminal connector which electrically connects the various electrodes and conductors within the lead body to a pulse generator and signal sensor 109. The pulse generator and signal senor 109 contains electronics to sense various electrical signals of the heart and also produce current pulses for delivery to the heart 101.

Figure 2:
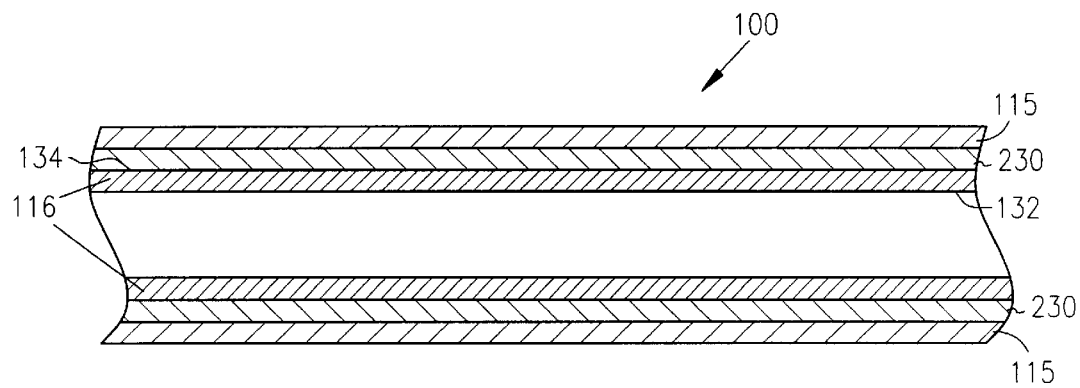
FIG. 2 is a cross-section of a lead assembly constructed in accordance with one embodiment.
Figure 3:
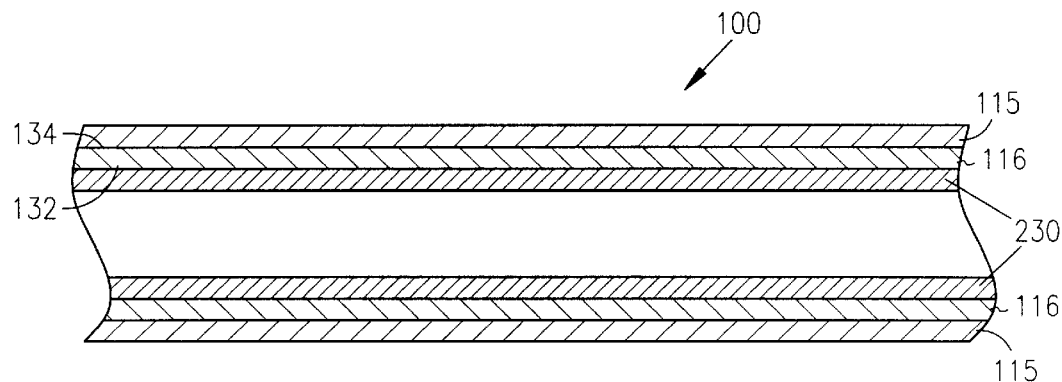
FIG. 3 is a cross-section of a lead assembly constructed in accordance with one embodiment.

The lead 100 includes a lead body 115, an elongate conductor 116 (FIGS. 2 and 3) contained within the lead body 115, and at least one electrode 120 coupled with the lead 100. The at least one electrode 120 is electrically coupled with the elongate conductor 116 (FIGS. 2 and 3). The lead body 115 is includes a biocompatible insulating material. Optionally, the elongate conductor 116 comprises a coiled conductor and defines a lumen therein and thereby is adapted to receive a stiffening stylet that extends through the length of the lead 100.

The stylet is used to stiffen the lead 100, and is manipulated to facilitate the insertion of the lead 100 into and through a vein and through an intracardiac valve to advance the distal end 102 of the lead 100 into, for example, the ventricle of the heart 101. A stylet knob is coupled with the stylet for rotating the stylet, advancing the conductor into tissue of the heart, and for manipulating the lead 100. Alternatively, the elongate conductor 116 comprises a cable conductor.

FIG. 2 illustrates a cross-section of the lead shown in FIG. 1, including the lead 100, and/or the lead 100 and the pulse generator and signal sensor 109. The lead 100 is used to chronically stimulate the heart 101, such that the lead 100 is implanted on or about the heart 101 for long periods of time. As mentioned above, the lead body 115 includes a covering of insulation. The lead 100 further includes a layer of echogenic material 230, where the lead body 115 completely encapsulates the layer of echogenic material 230.

The layer of echogenic material 230 is disposed directly on or in the conductor 116. The conductor 116 is defined in part by an inner surface 132 and an outer surface 134. As shown in FIG. 2, the layer of echogenic material 230 is disposed directly on the outer surface 134 of the conductor 116. Alternatively, as shown in FIG. 3, the layer of echogenic material 230 is disposed directly on the inner surface 132 of the conductor 116.

Figure 4:
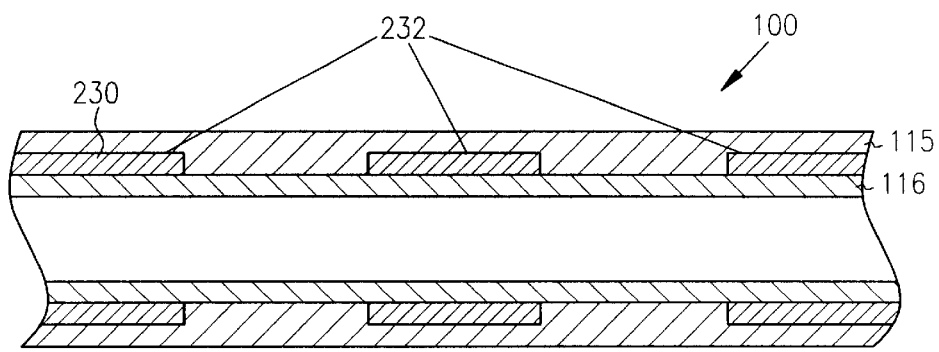
FIG. 4 is a cross-section of a lead assembly constructed in accordance with another embodiment.

The layer of echogenic material 230 optionally extends the full length of the lead 100, from the proximal end 104 to the distal end 102 of the lead body 115. Alternatively, the layer of echogenic material 230 extends for only a portion of the lead 100. In another option, as illustrated in FIG. 4, the echogenic is disposed on more than one portion of the length of the lead, where multiple portions 232 of echogenic material are disposed within the lead body 115. Optionally, the multiple portions 232 of echogenic material 230 are disposed directly on the conductor 116.

Figure 5:
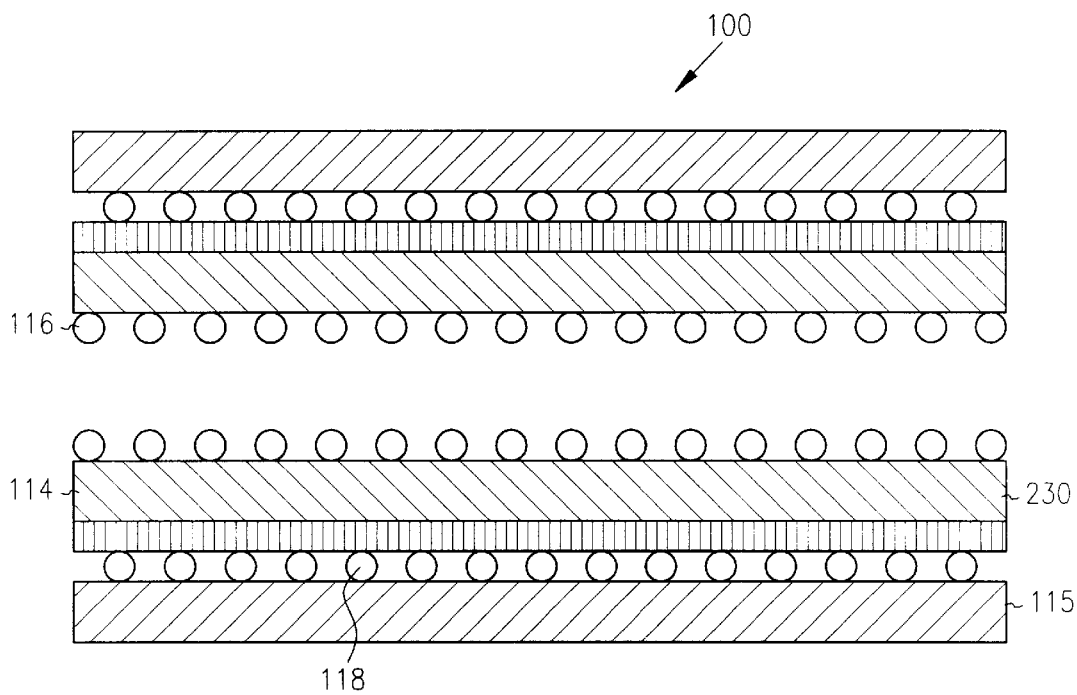
FIG. 5 is a cross-section of a lead assembly constructed in accordance with one embodiment.
Figure 6:
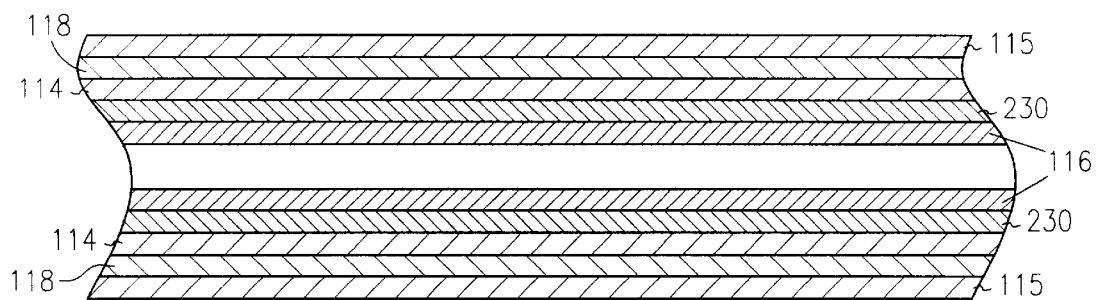
FIG. 6 is a cross-section of a lead assembly constructed in accordance with one embodiment.

FIG. 5 illustrates another alternative of the lead 100. As mentioned above, the lead body 115 includes a covering of insulation, and a conductor 116. The lead 100 further includes a second conductor 118, and an inner layer of insulation 114, where the inner layer of insulation 114 surrounds the conductor 116, and the lead body 115 surrounds the second conductor 118. The inner layer of insulation 114 is disposed between the conductor 116 and the second conductor 118. The lead 100 further includes a layer of echogenic material 230. The lead body 115 completely encapsulates the layer of echogenic material 230, where the layer of echogenic material 230 is disposed between the conductor 116 and the second conductor 118. The layer of echogenic material 230 is optionally disposed directly on the conductor 116. In another option, the layer of echogenic material 230 is disposed between the conductor 116 and the inner layer of insulator 114, as shown in FIG. 6. The layer of echogenic material 230 optionally extends the full length of the lead 100, from the proximal end 104 to the distal end 102 of the lead body 115. Alternatively, the layer of echogenic material 230 extends for only a portion of the lead 100, or is disposed on multiple portions, as discussed above.

Figure 7:
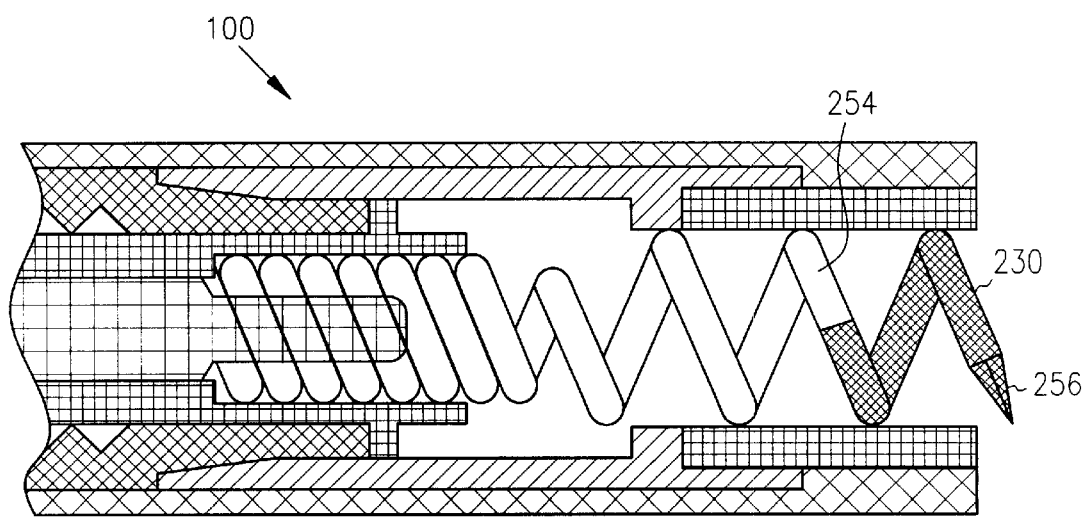
FIG. 7 is a cross-section of a lead assembly constructed in accordance with one embodiment.

FIG. 7 illustrates yet another option, where the lead 100 includes a helix 254 forming an active fixation device. The layer of echogenic material 230 is disposed on at least a portion of the helix 254. Optionally, the layer of echogenic material 230 is disposed at the distal tip 256 of the helix 254. The echogenic material 230 also is optionally disposed on two or more portions of a length of the lead 100.

Figure 8:
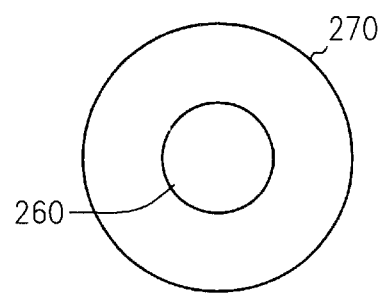
FIG. 8 is a cross-section of a portion of a lead assembly constructed in accordance with one embodiment.

The conductor 116 and/or the second conductor 118 are comprised of one or more filars 290. As shown in FIG. 8, each filar 260 optionally includes a layer of echogenic material 270. It should be noted that the filar 290 of FIG. 8 can be incorporated into any of the above described leads, or leads not described herein.

The layer of echogenic material 230 comprises, in one option, an echogenic coating. The echogenic coating, for use with the above discussed embodiments, optionally comprises any one of the following: a porous coating, a metallic coating, or a metal oxide coating. Alternatively, the layer of echogenic material 230 is created by surface texturing. In yet another option, the layer of echogenic material 230 is formed by mixing additives into the lead body 115 or inner insulator, where the additives are of lower or higher density than the component in which the additive is mixed. Examples of additives include, but are not limited to, metal powders, metal oxide powders, hollow glass microspheres, and various forms of carbon particles.

Advantageously, the above described lead provides a layer of echogenic material which provides a cost effective alternative to monitoring an implanted medical device, such as a lead. The echogenic material also allows the lead to be monitored safely, without risk to patients having sensitive medical conditions. Having the echogenic material disposed directly on the conductor allows for the location of the lead or medical device to be monitored more accurately. In addition, the layer of echogenic material is encapsulated by the lead body, such that the exposed blood and tissue contact surfaces of the lead remain unaffected from long-term biocompatibility and biostability.

It is to be understood that the above description is intended to be illustrative, and not restrictive. It should be noted that features of the various above-described embodiments may be interchanged to form additional combinations. Many other embodiments will be apparent to those of skill in the art upon reviewing the above description. For instance, the layer of echogenic material as described above can be incorporated into a variety of medial devices and a variety of leads. The scope of the invention should, therefore, be determined with reference to the appended claims, along with the full scope of equivalents to which such claims are entitled.

What is claimed is:

1. A lead assembly comprising:
    a flexible lead body extending from a proximal end to a distal end, the lead body including at least one conductor disposed therein, the flexible lead body including an outer surface;
    a first layer of echogenic material completely encapsulated by the flexible lead body;
    an electrode assembly including at least one electrode electrically coupled with the conductor;
    the first layer of echogenic material is disposed directly on or in the conductor at a first location; and
    a second layer of echogenic material disposed directly on or in the conductor at a second location.

2. The lead assembly as recited in claim 1, wherein the first layer of echogenic material comprises an echogenic coating.

3. The lead assembly as recited in claim 2, wherein the echogenic coating comprises a porous coating.

4. The lead assembly as recited in claim 2, wherein the echogenic coating comprises a metallic coating.

5. The lead assembly as recited in claim 2, wherein the echogenic coating comprises a metal oxide coating.

6. The lead assembly as recited in claim 1, wherein the conductor is a coiled conductor coil having an inner surface, and the first layer of echogenic layer is disposed within the conductor directly on the inner surface.

7. The lead assembly as recited in claim 1, further comprising an inner layer of insulator, and the first layer of echogenic material is disposed between the conductor and the inner layer of insulator.

8. The lead assembly as recited in claim 1, wherein the conductor comprises one or more filars, each filar having an outer filar surface, the first layer of echogenic material disposed directly on at least a portion of the outer filar surface.

9. The lead assembly as recited in claim 1, wherein echogenic material is disposed on three or more portions of a length of the lead.

10. The lead assembly as recited in claim 1, wherein the conductor includes a helix forming an active fixation device disposed at the distal end of the lead body, wherein the second layer of echogenic material is disposed on the helix.

11. A lead assembly comprising:
    a flexible lead body extending from a proximal end to a distal end, the lead body including at least one conductor disposed therein, the flexible lead body including an outer surface;
    a first layer of echogenic material disposed within the outer surface of the lead body; and
    an electrode assembly including at least one electrode electrically coupled with the conductor;
    wherein the conductor comprises one or more filars, each filar having an outer filar surface, the first layer of echogenic material disposed directly on at least a portion of the outer filar surface at a first location; and
    a second layer of echogenic material disposed directly on or in the conductor at a second location that is different than the first location.

12. The lead assembly as recited in claim 11, wherein the first layer of echogenic material comprises an echogenic coating.

13. The lead assembly as recited in claim 12, wherein the echogenic coating comprises a porous coating.

14. The lead assembly as recited in claim 12, wherein the echogenic coating comprises a metallic coating.

15. The lead assembly as recited in claim 12, wherein the echogenic coating comprises a metal oxide coating.

16. The lead assembly as recited in claim 11, further comprising an inner layer of insulator, and the first layer of echogenic material is disposed between the conductor and the inner layer of insulator.

17. The lead assembly as recited in claim 11, wherein the first and second layer of echogenic material extend from the proximal end to the distal end of the lead body.

18. The lead assembly as recited in claim 11, wherein the echogenic material is disposed on three or more portions of a length of the lead.

19. The lead assembly as recited in claim 11, wherein the conductor includes a helix forming an active fixation device disposed at the distal end of the lead body, wherein the first layer of echogenic material is disposed on at least a portion of the helix.

20. A lead assembly comprising:
    a flexible lead body extending from a proximal end to a distal end, the lead body including at least one conductor disposed therein, the conductor including a conductor outer surface;
    a layer of echogenic material disposed on at least a portion of the conductor outer surface, wherein the echogenic material is disposed on two or more portions of a length of the lead; and
    an electrode assembly including at least one electrode electrically coupled with the conductor.

21. The lead assembly as recited in claim 20, wherein the conductor includes a helix forming an active fixation device disposed at the distal end of the lead body, wherein the echogenic material is disposed on the helix.

* * * * *